[19] United States Patent
Gaston

[11] 4,378,025
[45] Mar. 29, 1983

[54] TECHNIQUES FOR PREPARING PACKAGING AND APPLYING COSMETIC PRODUCTS

[75] Inventor: Bontemps R. Gaston, Paris, France

[73] Assignee: Etablissement Troco, Vaduz, Liechtenstein

[21] Appl. No.: 138,335

[22] Filed: Apr. 8, 1980

[30] Foreign Application Priority Data

Apr. 10, 1979 [FR] France .................. 79 09003

[51] Int. Cl.³ ............................................ A45D 40/30
[52] U.S. Cl. ................................................ 132/88.5
[58] Field of Search ............... 132/88.5, 88.7; 249/92; 128/303.1, 399, 400, 402, 403

[56] References Cited

U.S. PATENT DOCUMENTS

| | | |
|---|---|---|
| 2,621,786 | 12/1952 | Schnack .................................. 401/86 |
| 2,718,126 | 9/1955 | Ball ........................................ 128/399 |
| 2,946,207 | 7/1960 | Hulterstrum ............................ 249/92 |
| 3,168,895 | 2/1965 | Okuhara ................................. 128/399 |
| 3,411,463 | 11/1968 | Mosergs ................................. 249/92 |
| 3,743,720 | 7/1973 | Fosker .................................... 424/92 |
| 4,239,175 | 12/1980 | Straubinger ............................ 249/92 |

FOREIGN PATENT DOCUMENTS 2128265 3/1971 France .

Primary Examiner—G. E. McNeill

[57] ABSTRACT

The cosmetic products of the invention are characterized by the fact that they are in the form of deep-frozen blocks or cakes, directly applicable to the skin and each allowing multiple applications, the vasoconstrictive action of the cold being added to the action properly speaking of the cosmetic substances, thus ensuring rapid penetration thereof into the epiderm.

7 Claims, 4 Drawing Figures

U.S. Patent  Mar. 29, 1983  4,378,025
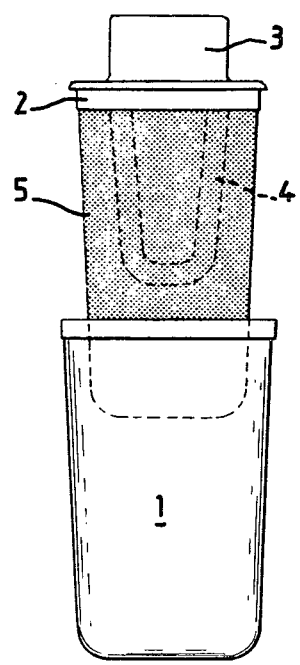
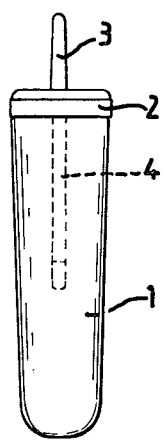
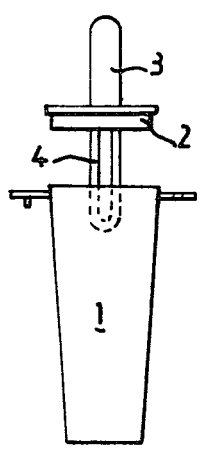
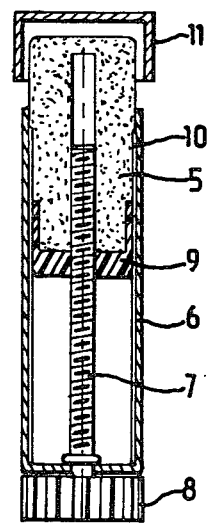

TECHNIQUES FOR PREPARING PACKAGING AND APPLYING COSMETIC PRODUCTS

BACKGROUND OF THE INVENTION

The present invention applies generally to all products having a cosmetic activity, not only those which are formulated from products of synthesis but also those which are based on natural components of animal, vegetable or mineral origin.

In accordance with the invention, a new and original method is proposed for applying cosmetic substances to the skin, which involves a special process for manufacturing and packing these substances.

There will be outlined herebelow, for different types of cosmetic compositions, problems of preparation and preservation which may arise and which the present invention resolves.

The creators of cosmetic, perfumery and hygiene products are frequently limited, in the conception of their formulae, by the impossibility of maintaining stable in time the mixtures or emulsions of substances whose properties they are attempting to associate so as to obtain a product having the desired characteristics.

Often, certain mixtures of fatty substances, particularly beneficial for the skin, do not have the texture or the consistency desirable at ambient temperature and the formulator must, in order to harden them, raise the melting point of the mixture by adding natural or synthetic waxes whose presence is not justified from the efficiency point of view.

Similarly, emulsions, widely used in cosmetology, require in order to remain stable the presence of emulsifiers in considerable quantities, which is not always desirable for the dermatological quality of the finished product.

Finally, whether it is a question of mixtures of fatty substances or even of emulsions, the raw materials used very often become rancid by oxidisation in contact with the air, at ambient temperature. This can at present be overcome by adding an anti-oxidizing agent and preserving agents, products which are more and more criticized and brought under regulation.

The present invention aims at providing the formulator with the possibility of maintaining in a stable condition physical systems which are not so in usual conditions of use for users.

We will also examine the particular case of cosmetic substances taken from the foetal pockets of animals.

Thus French Pat. No. 2 336 121 in the name of Raymond BONTEMPS relates to a fresh cosmetic product of foetal origin free from any excipient and preserving agent, consisting in a pure foetal substance such as the liver, the placenta, the mesenchyma, the thymus or the amnion etc. or in the association of these substances, these latter, taken from an animal, reduced to a puree and possibly associated, being packed at a temperature of about $-80°$ C.

Some of these products of foetal origin are in fact biogens, i.e. aspecific cells (ADN and ARN based) which are intended to create living matter and which must be applied to the skin while they are still in fresh condition, i.e. as if they had just been taken from the foetus.

In accordance with the teaching of the above-mentioned patent, in use said substances are thawed, and there is possibly incorporated therein a perfume and/or an isotonic liquid such as a physiological serum and/or a substance penetrating into the skin, in the proportion of 1 to 30%.

These preparations are used in cosmetology as masks or massaging products and give every satisfaction.

SUMMARY OF THE INVENTION

The present invention enables however the conditions of use of these cosmetic products of foetal origin to be further simplified while further increasing their efficiency.

The cosmetic products according to the present invention are essentially characterized by the fact that they are in the form of deep-frozen blocks or cakes, directly applicable to the skin and each permitting multiple applications, the vasoconstrictive action of the cold adding itself to the action properly speaking of these cosmetic substances, thus ensuring their rapid penetration into the epiderm.

It will be very easy to preserve these blocks or cakes at a low temperature in their deep-freeze moulds, made for example from metal or a plastic material. They may also be preserved removed from the mould, the important thing being that the chain of cold is not broken from manufacture to use.

Furthermore, in accordance with the present invention, means will also be provided for supporting the deep-frozen blocks so as to facilitate their use.

For example, the blocks, parallelepipedic, in the form of a truncated cone or in any other form, will be moulded around supports (sticks for example) made from wood, plastic material or similar, whose ends projecting from the block will enable them to be easily handled.

Preferably, each of these supports will be made integral with a lid of the mould. The user will thus be able to withdraw the deep-frozen block from its mould without contact with the cosmetic substance.

By way of variation, the deep-frozen block may be presented in a cylindrical case of the lip-stick or make-up type or else of the solid deodorant type, the user causing the upper end of the block (stick) to come out of the case for each application.

The process for packing these blocks or cakes, to which the present invention also relates, consists in pouring or compressing in appropriate moulds the chosen cosmetic substance or the chosen association of cosmetic substances, and in cooling them rapidly and intensively to complete deep-freeze, i.e. between $-25°$ C. and $-80°$ C. (dry ice).

In the case of cosmetic products other than pure foetal substances and the mixtures thereof, the mixture, emulsion or suspension of the raw materials will have been previously effected, if need be, by appropriate mechanical means (turbines, mixers, ultrasounds) while maintaining the mixture of the constituents at a temperature close to the limit of the solidification point thereof, the mixture being poured as soon as homogenization is sufficient.

The blocks of cosmetic substances thus formed may be preserved indefinitely at their preparation temperature; brought to about $-10°$ C. for use they may be still kept for some time (about a month) at this temperature without losing their efficiency.

Thus, the user may easily preserve cosmetic blocks in his deep-freeze or in the compartment of his refrigerator where ice is formed.

The application of a frozen block to the face leads to developing on the skin a film formed in general exclusively of the active substance, the block melting at the surface when it is at ambient temperature. The active substance presents at that moment maximum efficiency because, on the one hand, of the direct action of the preserved substances in the fresh condition and, on the other hand, because of its rapid penetration into the skin by vasoconstrictive effect, the contraction of the muscular fibers of the vessels of the epiderm ensuring "imprisonment" of the fine particles of cosmetic substance.

After each application of the block to his skin, the user places it in his deep-freeze until it is exhausted. There is never intermediate handling (contact of the cosmetic product with the hands), the deep-frozen block never loses its efficiency.

This application technique is particularly advantageous for cosmetic substances of foetal origin for which it is important that they keep exactly all the properties which they possessed at the moment when they were taken.

The interesting foetal substances are those which were mentioned above, as well as allantoid liquid, Meckel's cartilage, Wharton's jelly and all the possible associations, with if necessary physiological serum, this latter acting as an active substance.

Allantoid liquid is preferred, possibly associated with amnion, with placenta and/or with liver as the following two examples show:

EXAMPLE 1

Pure allantoid liquid (nutritive product for the foetus) is sterilely taken from a bovine foetal pocket, by means of a closed circuit pump, this liquid being immediately placed in moulds, also sterilized beforehand.

This operation will be carried out under laminar flux (i.e. an air overpressure in the room) a short time after the animal has been slaughtered (on average three hours).

The moulds filled with substance are lowered very rapidly to a temperature of $-80°$ C., so as to preserve all the biochemical formula and amin-acids which are contained therein.

EXAMPLE II

A preparation may also be made with, for example, 300 g of placenta, 200 g of liver, (pigmentation) 500 g of allentoids and 300 g of physiological aqueous solution. These substances will be passed through the mixer and filtered then placed in moulds and deep-frozen, still within a time not exceeding three hours after being taken, in the same conditions as before.

In the case of the other cosmetic substances, an appropriate formulation allows a product to be obtained melting and unctuous in contact with the skin having a texture close to that of an ice-cream.

The advantages of this process are the following:
possibility of associating non miscible constituents at ambient temperature,
possibility of reducing very considerably and even totally omitting auxiliary agents of stability, such as emulsifiers, anti-oxidizing agents and preserving agents.
no restriction in use of non saturated fatty substances particularly beneficial for the skin and whose rapid peroxidization at ambient temperature makes them difficult to use,
presentation in solid and stable form of a solid product which assumes its consistency of use in contact with the skin.

By way of non limiting examples, the following preparation formulae may be mentioned which, normally, are not stable in time at ambient temperature and which may be presented in the form of solid deep-frozen cakes by using a manufacturing process in accordance with the invention:

|  |  | A | B | C | D |
|---|---|---|---|---|---|
| PHASE I | Beeswax | 5.00 | 5.00 | 5.00 | 0 |
|  | Stearic acid | 2.00 | 3.00 | 3.00 | 12.00 |
|  | Cetyl alcohol | 3.00 | 3.00 | 3.00 | 0 |
|  | Soya lecithin | 2.00 | 0 | 0 | 0 |
|  | Soft almond oil | 5.00 | 7.00 | 7.00 | 0 |
|  | Vaseline oil | 0 | 0 | 0 | 48.00 |
| PHASE II | Reticulated polyacrylic acid (Molecular weight 1,000,000 to 4,000,000) | 1.60 | 1.60 | 0 | 0 |
|  | Carraghenate | 0 | 0 | 1.60 | 0 |
|  | Deionized water | 58.10 | 69.40 | 69.40 | 33.00 |
|  | Preserving agent | 0.30 | 0 | 0 | 0 |
| PHASE III | Amniotic liquid | 10.00 | 5.00 | 5.00 | 0 |
|  | Allentoid liquid | 10.00 | 5.00 | 5.00 | 5.00 |
|  | Tissue extract | 1.00 | 1.00 | 1.00 | 0 |
|  | Liver extract | 1.00 | 0 | 0 | 1.00 |
|  | Spleen extract | 1.00 | 0 | 0 | 1.00 |
| PHASE IV | Perfume | Q.S. | Q.S. | Q.S. | Q.S. |

The following mode of operation may advantageously be used.

(1) The raw materials of Phase I are weighed, melted and mixed by means of a propeller or turbine agitator in a receptacle capable of being then cooled to $-30°$ C. by means of an appropriate device. This phase is maintained at about 60° C.

(2) The constituents of Phase II are weighed and mixed at ambient temperature with a propeller agitator at a moderate speed. In the case of formula A, it may be necessary to previously heat the deionized water to about 80° C. so as to dissolve the preserving agent then to cool the solution to about 50° C. before introducing the polyacrylic acid. In the case of formula D, for phase II, it is sufficient to weigh the deionized water, since this raw material is the only component of this phase.

(3) Phase II is heated to 60° C.

(4) Phase II is poured in phase I maintained at 60° C., and the phases are mixed with rapid agitation by turbine or propeller.

(5) Refrigeration of the mixture is begun with agitation.

(6) When the temperature has been lowered to about 30° C., the constituents of phase III, previously weighed, are added to the mixture (phase I + phase II)

(7) As soon as the mixture is homogeneous, and before it has solidified, it is poured into moulds of appropriate shape previously cooled to 0° C.

(8) The moulds are immediately placed in a deep-freeze and maintained at temperatures between $-25°$ C. and $-80°$ C.

(9) When the cakes are solidified, they are removed from the mould and are preserved in the deep-freeze maintained at temperatures between $-25°$ C. and $-80°$ C.

In the accompanying drawing, three possible examples of moulds are shown for cosmetic cakes in accordance with the invention.

FIGS. 1 and 2 show a substantially parallelpipedic mould, respectively in elevation and in profile, FIG. 3 shows a truncated cone shaped mould and FIG. 4 a receptacle for a stick.

Moulds 1 (FIGS. 1 and 2) may be closed by a lid 2 having on the outside a tongue 3 for grasping and on the inside a support 4 for the deep-frozen cosmetic block 5.

In the case of the stick, the deep-frozen block 5 may be caused to project from its cylindrical receptacle 6 in the center of which is disposed a screw 7 operable by means of a knob 8 situated at the base of cylinder 6. Block 5 is maintained in position at its lower part by a base 9 and it is guided in its vertical movement by inner vertical ribs 10 of cylinder 6. The whole is protected by means of a cap 11.

What is claimed is:

1. Cosmetic products in the form of deep-frozen blocks or cakes, directly applicable to the skin and intended to penetrate the skin upon application thereto, and each allowing multiple applications, the vasoconstrictive action of the cold being added to the action of these cosmetic substances, thus ensuring their rapid penetration into the epiderm, and wherein said block or cakes are based on pure foetal substances chosen from liver, placenta, mesenchyma, thymus, amnion, allantoid liquid, Meckel's cartilage, Warton's jelly or based on mixtures of these substances.

2. A process for manufacturing the cosmetic products defined in claim 1, wherein said foetal substances are taken sterilely, then crushed and filtered and if necessary associated, these operations being carried out under laminary flux, said products being intended to be preserved and distributed in the deep-frozen condition, and the chosen cosmetic substance or the chosen association of cosmetic substances being poured or compressed in appropriate moulds and rapidly and intensively refrigerated to complete deep-freeze, i.e. between $-25°$ C. and $-80°$ C. (dry ice), the blocks or cakes being brought up to about $-10°$ C. and preserved at this temperature for use.

3. Cosmetic products in the form of deep-frozen blocks or cakes, directly applicable in a cold condition to the skin and intended to penetrate the skin upon application thereto, and each allowing multiple applications, the vasoconstrictive action of the cold being added to the action of these cosmetic substances, thus ensuring their rapid penetration into the epiderm, and wherein said block or cakes are based on pure foetal substances chosen from liver, placenta, mesenchyma, thymus, amnion, allantoid liquid, Meckel's cartilage, Warton's jelly or based on mixtures of these substances.

4. A method of using a cosmetic product as claimed in claim 3, comprising applying said product directly to the skin in its deep-frozen state, without preliminary thawing, at a temperature of about $-10°$ C.

5. A cosmetic product adapted to be directly applied to the skin, characterized in that a skin wrinkle removing product which is intended to be absorbed into a user's skin upon application thereto is in the form of a deep-frozen block or cake based on pure foetal substances chosen from liver, placenta, mesenchyma, thymus, amnion, allantoid liquid, Meckel's cartilage, Wharton's jelly or based on mixtures of these substances, and in that means is provided for grasping said deep-frozen block or cake without having any contact of the cosmetic product with the hands.

6. A cosmetic product as claimed in claim 5, wherein the block or cake additionally contains physiological serum, this latter acting as an active substance.

7. A process for preparing a cosmetic product as claimed in claim 5, in which said foetal substances are taken sterilely, then crushed and filtered and if necessary associated, these operations being carried out under laminary flux, said process comprising the steps of pouring or compressing in a mould the chosen cosmetic substance or the chosen association of cosmetic substances and of rapidly and intensively refrigerating it to complete deep-frozen between $-25°$ C. and $-80°$ C., the formed block or cake being brought up to about $-10°$ C. and preserved at this temperature for use.

* * * * *